(12) United States Patent
Westphal et al.

(10) Patent No.: US 10,994,042 B2
(45) Date of Patent: May 4, 2021

(54) HEATED AIR FRESHENER

(71) Applicant: S. C. JOHNSON & SON, INC., Racine, WI (US)

(72) Inventors: Nathan R. Westphal, Union Grove, WI (US); Kevin Harrity, Oak Creek, WI (US); Alex Mecker, Milwaukee, WI (US); Chris A. Koontz, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 469 days.

(21) Appl. No.: 15/005,490

(22) Filed: Jan. 25, 2016

(65) Prior Publication Data

US 2017/0209612 A1 Jul. 27, 2017

(51) Int. Cl.
*A61L 9/03* (2006.01)
*A01M 1/20* (2006.01)

(52) U.S. Cl.
CPC ............. *A61L 9/03* (2013.01); *A01M 1/2077* (2013.01); *A61L 2209/11* (2013.01); *A61L 2209/133* (2013.01); *A61L 2209/134* (2013.01); *A61L 2209/15* (2013.01)

(58) Field of Classification Search
CPC .......... A61L 9/03; A61L 9/037; A01M 1/2077
USPC ........ 392/390, 395, 404; 219/202, 267, 136; 422/125
See application file for complete search history.

(56) References Cited

U.S. PATENT DOCUMENTS

| | | | |
|---|---|---|---|
| 2,786,406 A | 3/1957 | White | |
| 2,898,649 A | 8/1959 | Murray | |
| 4,383,951 A | 5/1983 | Palson | |
| 4,574,181 A | 3/1986 | Spector | |
| 4,702,418 A | 10/1987 | Carter et al. | |
| 4,808,347 A | 2/1989 | Dawn | |
| 4,968,456 A | 11/1990 | Muderlak et al. | |
| 5,234,162 A | 8/1993 | Sullivan | |
| 5,342,584 A | 8/1994 | Fritz et al. | |
| 5,373,581 A * | 12/1994 | Smith | A01M 1/2077 219/202 |
| 5,394,506 A | 2/1995 | Stein et al. | |
| 5,439,100 A | 8/1995 | Gordon et al. | |
| 5,484,086 A | 1/1996 | Pu | |
| 5,605,308 A | 2/1997 | Quan et al. | |

(Continued)

FOREIGN PATENT DOCUMENTS

| | | |
|---|---|---|
| CN | 202173617 U | 3/2012 |
| CN | 103768638 A | 5/2014 |

(Continued)

OTHER PUBLICATIONS

Machine Translation for ES2255422, May 2018.*

(Continued)

*Primary Examiner* — Tu B Hoang
*Assistant Examiner* — Thomas J Ward
(74) *Attorney, Agent, or Firm* — Quarles & Brady LLP

(57) ABSTRACT

A volatile material dispenser that includes a housing, an electrical assembly that is received within the housing and includes a heater, and an adjustment assembly that is coupled to the housing and is configured to support a cartridge. The adjustment assembly is movable between a maximum output position, an intermediate output position, and an off position.

19 Claims, 14 Drawing Sheets

(56) References Cited

U.S. PATENT DOCUMENTS

| | | | |
|---|---|---|---|
| 5,788,931 | A | 8/1998 | Quintana |
| 5,833,929 | A | 11/1998 | Watson et al. |
| 5,903,710 | A | 5/1999 | Wefler et al. |
| 6,021,254 | A | 2/2000 | Hunter |
| 6,085,026 | A | 7/2000 | Hammons et al. |
| 6,085,027 | A | 7/2000 | Sexton |
| 6,090,349 | A | 7/2000 | Hirano |
| 6,095,153 | A | 8/2000 | Kessler et al. |
| 6,099,131 | A | 8/2000 | McCormack et al. |
| 6,135,431 | A | 10/2000 | Muhmel et al. |
| 6,197,263 | B1 | 3/2001 | Blount |
| 6,278,840 | B1 | 8/2001 | Millan |
| 6,285,830 | B1 | 9/2001 | Millan |
| 6,354,710 | B1 | 3/2002 | Nacouzi |
| 6,374,044 | B1* | 4/2002 | Freidel .................. A61L 9/03 239/34 |
| 6,413,476 | B1 | 7/2002 | Barnhart |
| 6,443,434 | B1 | 9/2002 | Vieira |
| 6,446,583 | B2 | 9/2002 | Prather |
| 6,466,739 | B2 | 10/2002 | Ambrosi et al. |
| 6,580,875 | B2 | 6/2003 | Rymer |
| 6,592,828 | B2* | 7/2003 | Quintana Munoz ........................ A01M 1/2077 392/390 |
| 6,644,507 | B2 | 11/2003 | Borut et al. |
| 6,661,967 | B2 | 12/2003 | Levine et al. |
| 6,782,194 | B2 | 8/2004 | Schneiderbauer |
| 6,796,340 | B1 | 9/2004 | Ferris et al. |
| 6,854,717 | B2 | 2/2005 | Millan |
| 6,859,615 | B2 | 2/2005 | Yip et al. |
| 6,862,403 | B2 | 3/2005 | Pedrotti et al. |
| 6,917,754 | B2 | 7/2005 | Pedrotti et al. |
| 6,920,282 | B2 | 7/2005 | He et al. |
| 6,931,202 | B2 | 8/2005 | Pedrotti et al. |
| 6,950,607 | B2 | 9/2005 | Yip et al. |
| 6,957,779 | B2 | 10/2005 | Joshi et al. |
| 6,996,335 | B2 | 2/2006 | Zobele |
| 7,082,259 | B2 | 7/2006 | Zobele |
| 7,141,215 | B2 | 11/2006 | Guan et al. |
| 7,188,780 | B2 | 3/2007 | Martens, III |
| 7,190,888 | B2 | 3/2007 | Wolf et al. |
| 7,209,650 | B2 | 4/2007 | Caserta et al. |
| 7,213,770 | B2 | 5/2007 | Martens, III et al. |
| 7,341,698 | B2 | 3/2008 | Pedrotti et al. |
| 7,350,720 | B2 | 4/2008 | Jaworski et al. |
| 7,389,943 | B2 | 6/2008 | Jaworski |
| 7,441,360 | B2 | 10/2008 | Christianson et al. |
| 7,462,329 | B2 | 12/2008 | Weller |
| 7,469,844 | B2 | 12/2008 | Conway et al. |
| 7,484,716 | B2 | 2/2009 | Morie et al. |
| 7,497,685 | B2 | 3/2009 | Kubicek et al. |
| 7,503,668 | B2 | 3/2009 | Porchia et al. |
| 7,534,406 | B2 | 5/2009 | Takemura |
| 7,544,331 | B1 | 6/2009 | Pettaway |
| 7,544,332 | B2 | 6/2009 | De Silva et al. |
| 7,548,684 | B2 | 6/2009 | Berrido et al. |
| 7,610,118 | B2 | 10/2009 | Schramm et al. |
| 7,651,666 | B2 | 1/2010 | Adair et al. |
| 7,824,627 | B2 | 11/2010 | Michaels et al. |
| 7,931,213 | B2 | 4/2011 | Walter et al. |
| 7,932,482 | B2 | 4/2011 | Norwood et al. |
| 7,938,338 | B2 | 5/2011 | Janakat et al. |
| 7,954,667 | B2 | 6/2011 | Furner et al. |
| 7,962,017 | B2 | 6/2011 | Viera |
| 7,980,486 | B2 | 7/2011 | Trent et al. |
| 8,005,349 | B2 | 8/2011 | Franco |
| 8,061,562 | B2 | 11/2011 | Carpenter et al. |
| 8,062,598 | B2 | 11/2011 | Bertassi et al. |
| 8,091,734 | B2 | 1/2012 | Furner et al. |
| 8,170,405 | B2 | 5/2012 | Harris |
| 8,196,902 | B1 | 6/2012 | Pystin |
| 8,197,761 | B1 | 6/2012 | Miller-Larry |
| 8,342,363 | B2 | 1/2013 | Carpenter et al. |
| 8,342,370 | B2 | 1/2013 | Ross et al. |
| 8,371,310 | B2 | 2/2013 | Brenneise |
| 8,371,740 | B2 | 2/2013 | Pestl et al. |
| 8,412,029 | B2 | 4/2013 | Browder et al. |
| 8,463,114 | B2 | 6/2013 | Fabrega |
| 8,498,524 | B2 | 7/2013 | Ruiz et al. |
| 8,662,480 | B1 | 3/2014 | Irvin |
| 8,678,233 | B2 | 3/2014 | Furner et al. |
| 8,718,454 | B2 | 5/2014 | Caserta et al. |
| 8,740,107 | B2 | 6/2014 | Marchetti et al. |
| 8,750,694 | B1 | 6/2014 | Porretta et al. |
| 8,765,063 | B1 | 7/2014 | Mazzilli |
| 8,783,510 | B2 | 7/2014 | Reynolds et al. |
| 8,787,739 | B2 | 7/2014 | Hsiao |
| 8,887,954 | B2 | 11/2014 | Carpenter et al. |
| 8,983,277 | B2 | 3/2015 | Hsiao |
| 8,983,278 | B2 | 3/2015 | Ruiz et al. |
| 8,983,279 | B2 | 3/2015 | Adair et al. |
| 8,999,259 | B2 | 4/2015 | King et al. |
| 9,031,392 | B2 | 5/2015 | Hsiao |
| 9,042,712 | B2 | 5/2015 | Irvin et al. |
| 9,144,621 | B1 | 9/2015 | Finlay |
| 9,259,750 | B2 | 2/2016 | Johnson et al. |
| 9,352,062 | B2* | 5/2016 | Klemm .............. A01M 1/2033 |
| 9,388,994 | B2 | 7/2016 | Hidaka et al. |
| 9,393,337 | B2 | 7/2016 | Gruenbacher et al. |
| 9,399,080 | B2 | 7/2016 | Irvin et al. |
| 9,408,936 | B2 | 8/2016 | Esses |
| 9,522,208 | B2 | 12/2016 | Esses |
| 9,877,510 | B2 | 1/2018 | Henry, Jr. |
| 9,999,250 | B2 | 6/2018 | Minskoff et al. |
| 2002/0176704 | A1 | 11/2002 | Roe |
| 2003/0138241 | A1 | 7/2003 | Pedrotti et al. |
| 2003/0206834 | A1 | 11/2003 | Chiao et al. |
| 2004/0009103 | A1 | 1/2004 | Westing |
| 2004/0190883 | A1 | 9/2004 | Kompara et al. |
| 2005/0175331 | A1 | 8/2005 | Tan et al. |
| 2005/0220664 | A1 | 10/2005 | Hitzler et al. |
| 2006/0000922 | A1 | 1/2006 | Martens |
| 2006/0032937 | A1 | 2/2006 | Caserta |
| 2006/0193610 | A1 | 8/2006 | Han |
| 2006/0193611 | A1 | 8/2006 | Ruiz Ballesteros et al. |
| 2006/0292110 | A1 | 12/2006 | Reinhardt |
| 2007/0183924 | A1 | 8/2007 | Morgan |
| 2007/0183981 | A1 | 8/2007 | Varanasi et al. |
| 2007/0257016 | A1 | 11/2007 | Jin et al. |
| 2007/0262166 | A1 | 11/2007 | Majerowski |
| 2008/0095522 | A1 | 4/2008 | Deflorian et al. |
| 2008/0277495 | A1 | 11/2008 | Duru |
| 2009/0041442 | A1 | 2/2009 | Rouse, Jr. |
| 2009/0078253 | A1 | 3/2009 | Bao |
| 2009/0196587 | A1 | 8/2009 | Cheung |
| 2009/0232710 | A1 | 9/2009 | Kinsey |
| 2009/0302019 | A1 | 12/2009 | Selenski et al. |
| 2010/0010908 | A1 | 1/2010 | Pasuplati et al. |
| 2010/0059602 | A1 | 3/2010 | Chiou et al. |
| 2010/0178042 | A1 | 7/2010 | Neumann et al. |
| 2010/0193599 | A1 | 8/2010 | Bulter et al. |
| 2010/0326280 | A1 | 12/2010 | Hicks |
| 2011/0132995 | A1 | 6/2011 | Perman |
| 2011/0134628 | A1 | 6/2011 | Pestl |
| 2011/0139810 | A1 | 6/2011 | Lee |
| 2012/0000989 | A1 | 1/2012 | Bordier |
| 2012/0018529 | A1 | 1/2012 | Gammon et al. |
| 2012/0201523 | A1 | 8/2012 | Tebe Poves et al. |
| 2012/0224995 | A1 | 9/2012 | McMinn |
| 2013/0049236 | A1 | 2/2013 | Garon et al. |
| 2014/0091487 | A1 | 4/2014 | Belongia |
| 2014/0112649 | A1 | 4/2014 | Irvin et al. |
| 2014/0126892 | A1 | 5/2014 | Hsiao |
| 2014/0145004 | A1 | 5/2014 | Westphal |
| 2014/0193764 | A1 | 7/2014 | Pizzini |
| 2014/0209698 | A1 | 7/2014 | Olchovy et al. |
| 2014/0209700 | A1 | 7/2014 | Olchovy et al. |
| 2014/0261408 | A1 | 9/2014 | DePiano et al. |
| 2014/0377130 | A1 | 12/2014 | Edwards et al. |
| 2015/0258289 | A1 | 9/2015 | Henry et al. |
| 2015/0320899 | A1 | 11/2015 | Soliz et al. |
| 2016/0015847 | A1 | 1/2016 | Irvin et al. |
| 2016/0022855 | A1 | 1/2016 | Esses |
| 2016/0022857 | A1 | 1/2016 | Esses |

(56) References Cited

U.S. PATENT DOCUMENTS

| | | |
|---|---|---|
| 2016/0067367 A1 | 3/2016 | Jin et al. |
| 2016/0107186 A1 | 4/2016 | Chao |
| 2016/0152117 A1 | 6/2016 | Backman et al. |
| 2016/0256585 A1 | 9/2016 | Esses |
| 2016/0279278 A1 | 9/2016 | Gruenbacher et al. |
| 2016/0325605 A1 | 11/2016 | Irvin et al. |
| 2016/0331913 A1 | 11/2016 | Bourque |
| 2017/0128608 A1 | 5/2017 | Hsiao |
| 2018/0064839 A1 | 3/2018 | Hsiao |
| 2018/0126022 A1 | 5/2018 | Hsiao |
| 2018/0126025 A1 | 5/2018 | Hsiao |

FOREIGN PATENT DOCUMENTS

| | | | | |
|---|---|---|---|---|
| CN | 105188777 A | 12/2015 | | |
| CN | 204951729 U | 1/2016 | | |
| DE | 202013101904 U1 | 6/2013 | | |
| EP | 0511853 A2 | 11/1992 | | |
| EP | 1175833 A1 | 1/2002 | | |
| ES | 2255422 | * | 9/2004 | ............... A61L 9/03 |
| ES | 2255422 A1 | 6/2006 | | |
| JP | 01060918 U | 4/1989 | | |
| JP | 04136082 U | 12/1992 | | |
| JP | 2002200154 A | 7/2002 | | |
| JP | 2003225293 A | 8/2003 | | |
| JP | 2004524864 A | 8/2004 | | |
| JP | 2004313004 A | 11/2004 | | |
| JP | 2010506577 A | 3/2010 | | |
| JP | 2010532170 A | 10/2010 | | |
| JP | 2015531621 A | 11/2015 | | |
| JP | S56020869 B | 11/2015 | | |
| KR | 20040043304 A | 5/2004 | | |
| NO | WO2007142851 A2 | 12/2007 | | |
| WO | 1997039778 A1 | 10/1997 | | |
| WO | 2003077961 A1 | 9/2003 | | |
| WO | 2004028574 A1 | 4/2004 | | |
| WO | 2005092399 A1 | 10/2005 | | |
| WO | 2007018402 A1 | 2/2007 | | |
| WO | 2007083042 A1 | 7/2007 | | |
| WO | 2011020491 A1 | 2/2011 | | |
| WO | 2013106982 A1 | 7/2013 | | |
| WO | 2014022164 A1 | 2/2014 | | |
| WO | 2014025720 A1 | 2/2014 | | |
| WO | 2014055478 A1 | 4/2014 | | |
| WO | 2014087173 A1 | 6/2014 | | |
| WO | 2015116934 A1 | 8/2015 | | |
| WO | 2016083165 A1 | 6/2016 | | |
| WO | 2016096272 A1 | 6/2016 | | |
| WO | 2016155333 A1 | 10/2016 | | |
| WO | 2016180663 A1 | 11/2016 | | |

OTHER PUBLICATIONS

International Search Report & Written Opinion, International Application No. PCT/US2017/012727, dated Dec. 5, 2017, 29 pages.
Non Final Office Action, U.S. Appl. No. 15/005,651 dated Nov. 3, 2017, 11 pages.
International Search Report & Written Opinion, International Application No. PCT/US2017/012862, dated Jun. 26, 2017, 11 pages.
International Search Report & Written Opinion, International Application No. PCT/US2017/018130, dated Jun. 2, 2017, 16 pages.
Grounds for Rejection issued in Chinese Application No. 201780027275. 6, dated Apr. 29, 2020, 11 pages.
First Office Action from corresponding Japanese Patent Application No. 2018-538830, dated Dec. 1, 2020 (6 pages).
First Office Action from corresponding Chinese Patent Application No. 201780019773.6, dated Nov. 12, 2020 (9 pages) (English translation unavailable).

* cited by examiner

HEATED AIR FRESHENER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to air fresheners with a replaceable refill, and more specifically, to air fresheners used in combination with a heat source.

2. Description of the Background of the Invention

Typical air fresheners, for example those used in an automobile, that are arranged to be used with a heat source include a heating element, a refill or cartridge that receives heat from the heating element, and vents that expel volatile emanated from the cartridge to the surrounding atmosphere. Some air fresheners are arranged to plug into a 12V power socket provided with most automobiles. The automobile's power is used to power the heating element.

However, some drawbacks exist with these types of air fresheners. Current air fresheners do not provide an adjustable fragrance, and offer no shut-off feature. Further, typical devices, and the cartridges used in them, vary in their length of life and fragrance intensity according to the time of day and year.

Therefore, a need exists for a heated air freshener that can control fragrance intensity, and provide a shut-off feature.

SUMMARY OF THE INVENTION

The present disclosure overcomes some of the aforementioned drawbacks by providing a heated air freshener that provides a simple to use interface that provides adjustable fragrance intensity, and a shut-off feature.

According to one aspect, an automobile air freshener includes a housing arranged to be received within a 12V power socket and an electrical system received within the housing and arranged to receive power from the 12V power socket. The electrical system includes a heater and a switch selectively powering the heater. An adjustment assembly is movable between an on position and an off position, and includes a cartridge holder configured to hold a cartridge. The adjustment assembly is arranged to actuate the switch when in the on position such that power is supplied to the heater. A lid includes a lid seal arranged to inhibit air flow to the cartridge when the adjustment assembly is in the off position.

According to another aspect, an adjustment assembly for an air freshener that is configured to interact with a heat source includes an adjustment ring that is graspable by a user and actuatable between a maximum output position, an intermediate output position, and an off position. A cartridge holder is arranged to hold a cartridge that includes a semi permeable membrane and a reservoir filled with an active ingredient. The cartridge is coupled to and movable with the adjustment ring along a cam profile such that when arranged in the maximum output position a maximum heat exchange rate between the heat source and the cartridge is achieved. When the adjustment ring is arranged in the off position, a minimum heat exchange rate between the heat source and the cartridge is achieved, and when the adjustment ring is arranged in the intermediate output position an intermediate heat exchange rate is achieved that is between the maximum heat exchange rate and the minimum heat exchange rate.

According to another aspect, a volatile material dispenser includes a housing, an electrical assembly that is received within the housing and that has a heater, and an adjustment assembly that is coupled to the housing and configured to support a cartridge. The adjustment assembly is movable between a maximum output position, an intermediate output position, and an off position.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
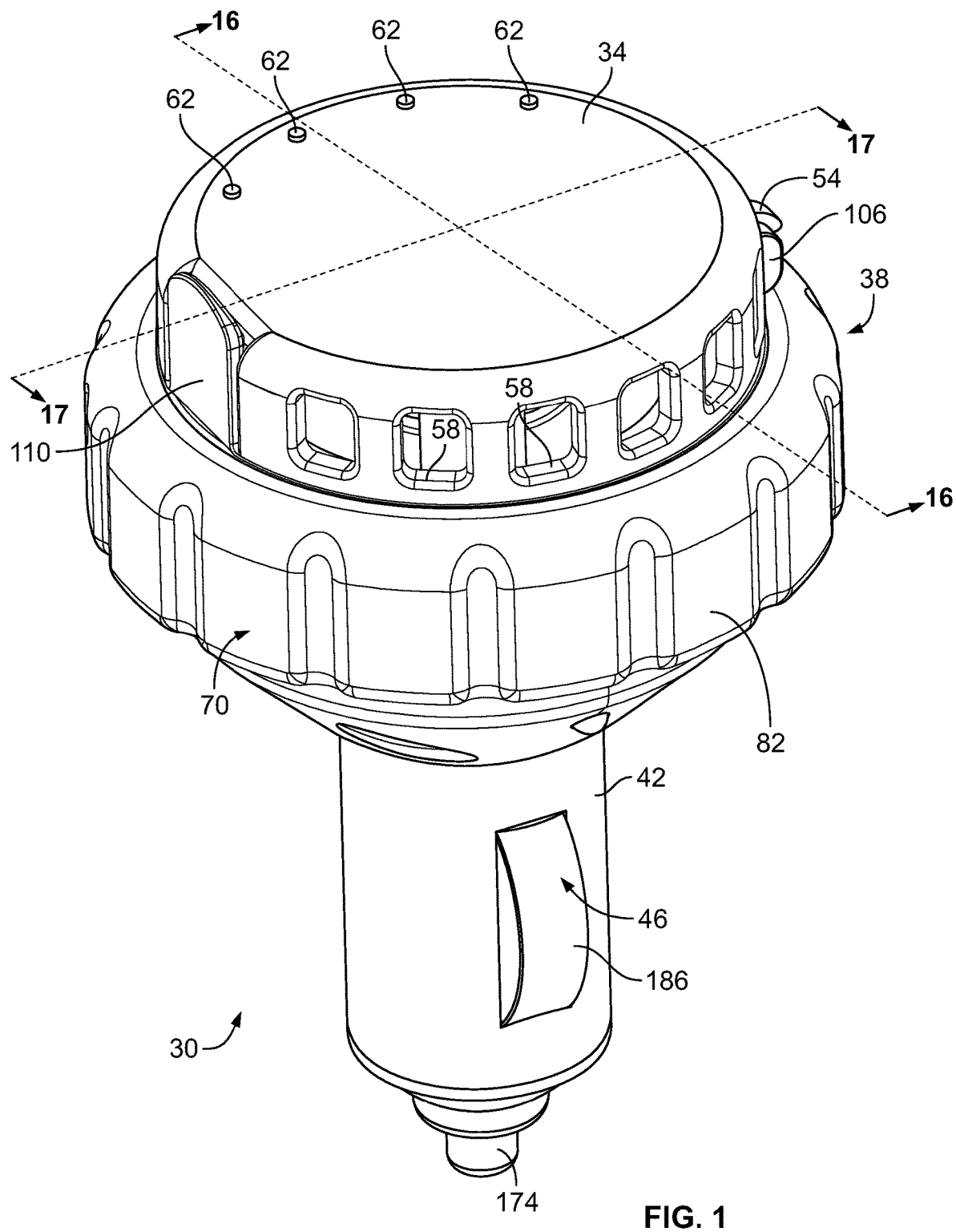
FIG. 1 is a top right isometric view of an air freshener according to one embodiment.
Figure 2:
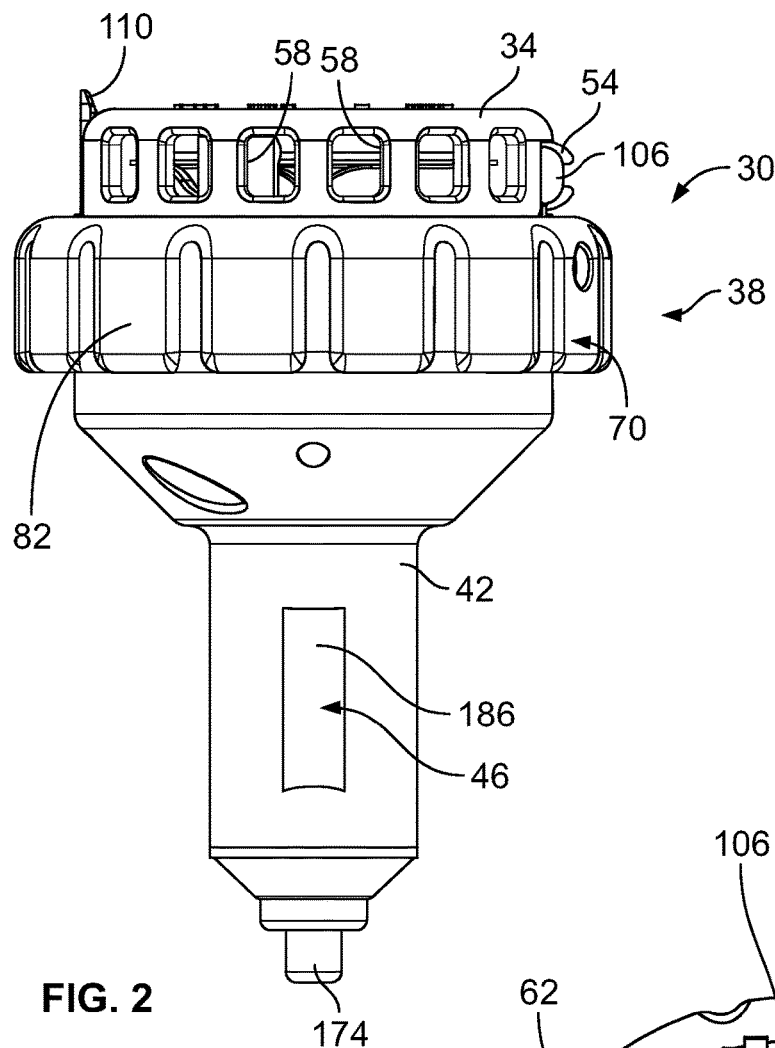
FIG. 2 is a side elevational view of the air freshener of FIG. 1.
Figure 3:
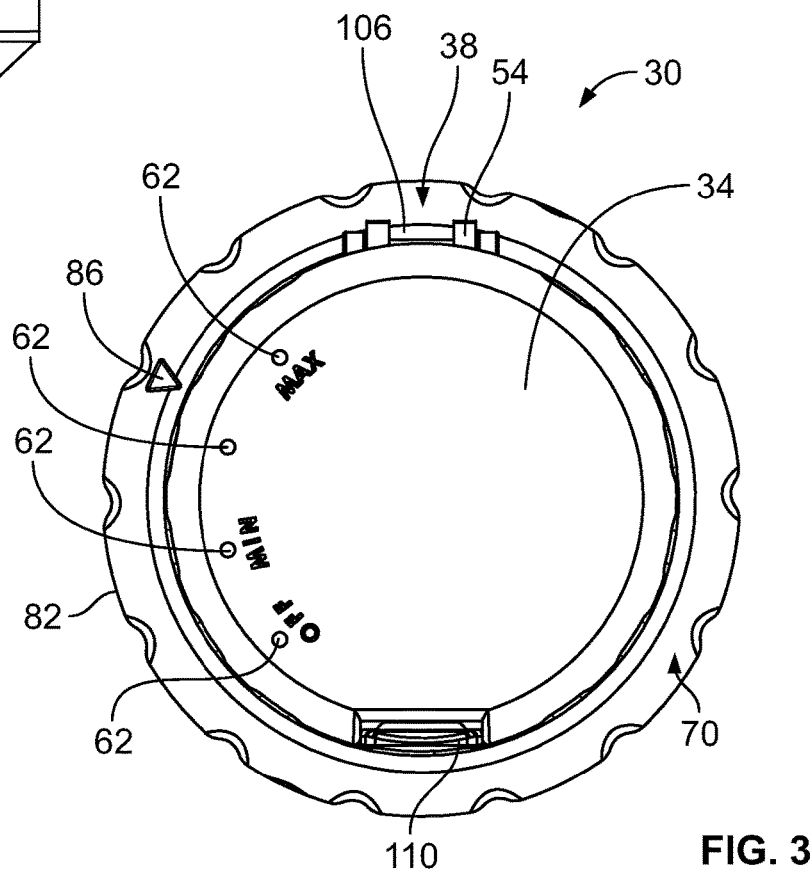
FIG. 3 is a top plan view of the air freshener of FIG. 1.

With reference to FIGS. 1-3, an air freshener 30 is shown. The air freshener 30 is a heated air freshener that may be used, for example, in an automobile. The air freshener 30 includes a lid 34, an adjustment assembly 38, a body 42, and an electrical system 46 that is received within the body 42.

Figure 4:
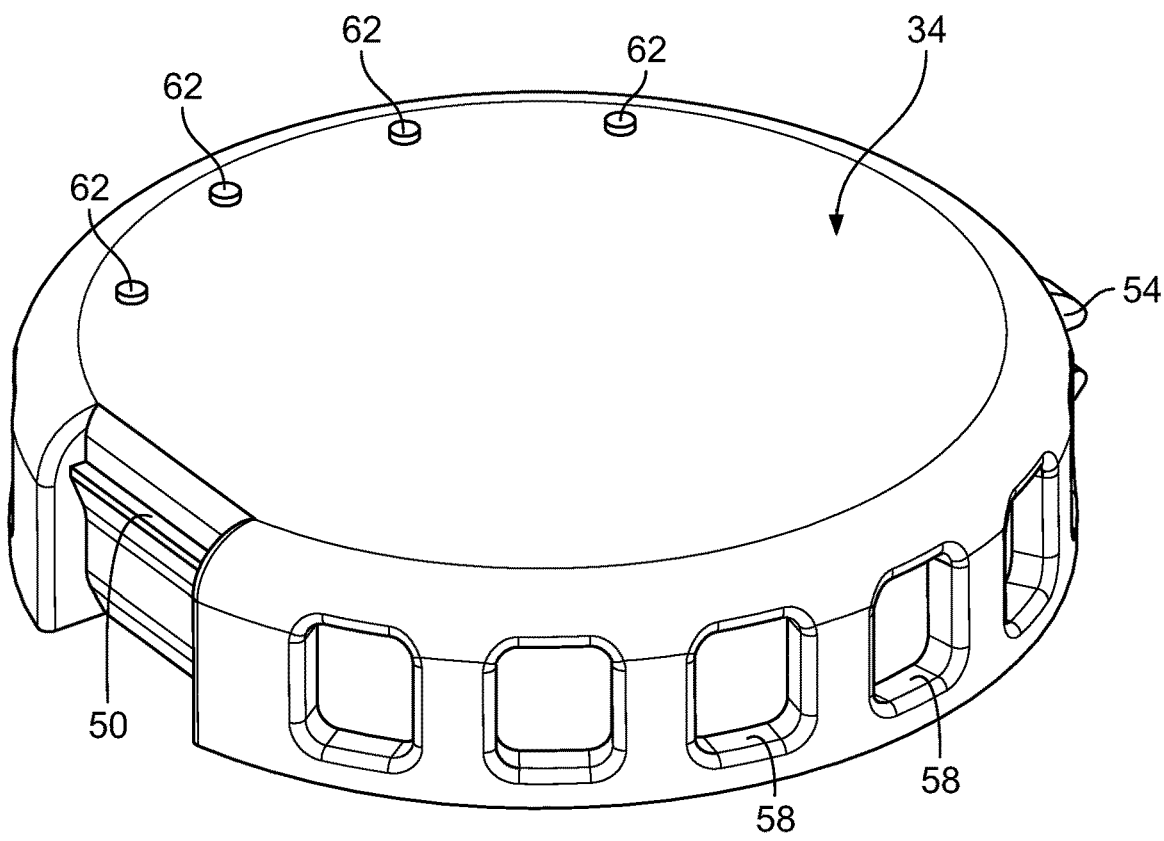
FIG. 4 is a top right isometric view of a lid of the air freshener of FIG. 1.
Figure 5:
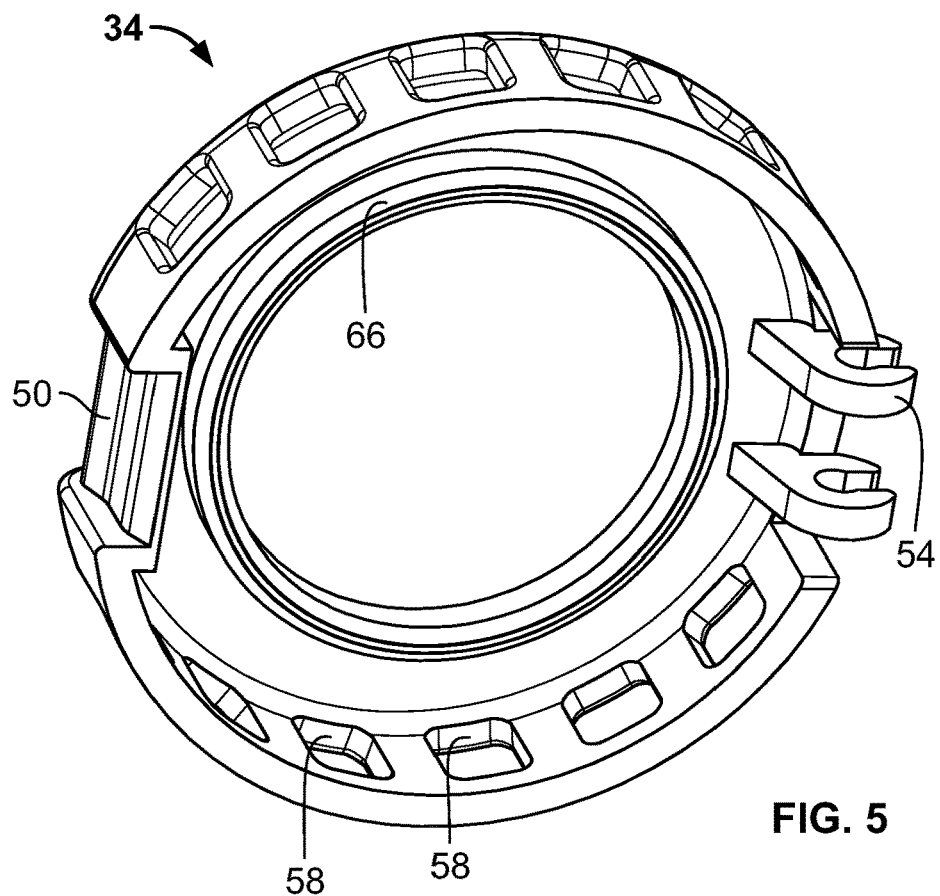
FIG. 5 is a bottom right isometric view of the lid of FIG. 4.

As shown in FIGS. 4 and 5, the lid 34 includes a lid latch 50, a hinge member 54, a plurality of vents 58, indicator marks 62, and a lid seal 66. The lid latch 50 is in the form of a protrusion and the hinge member 54 is in the form of two spaced apart hooks. The plurality of vents 58 are arranged radially around the lid 34 and are rectangularly shaped. The indicator marks 62 include an off mark, a minimum mark, a maximum mark, and an intermediate mark. In other embodiments, fewer or greater numbers of intermediate marks 62 may be included. Additionally, the indicator marks 62 may include a gradient, a two-dimensional image, or another kind of mark that denotes a range or levels. The illustrated lid seal 66 is in the form of a generally circular protrusion.

Figure 6:
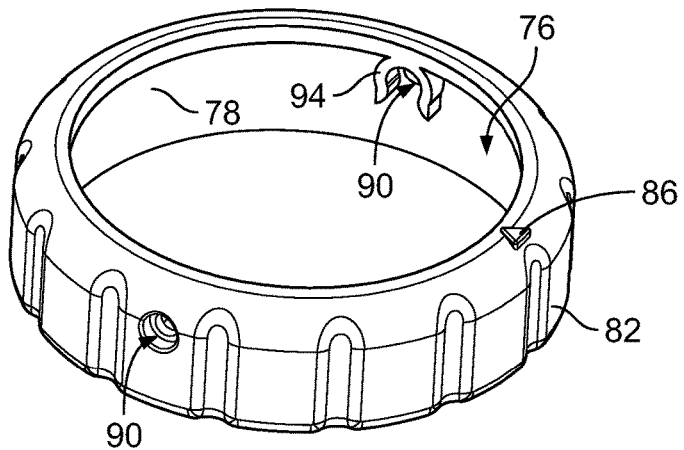
FIG. 6 is a top left isometric view of an adjuster of the air freshener of FIG. 1.
Figure 7:
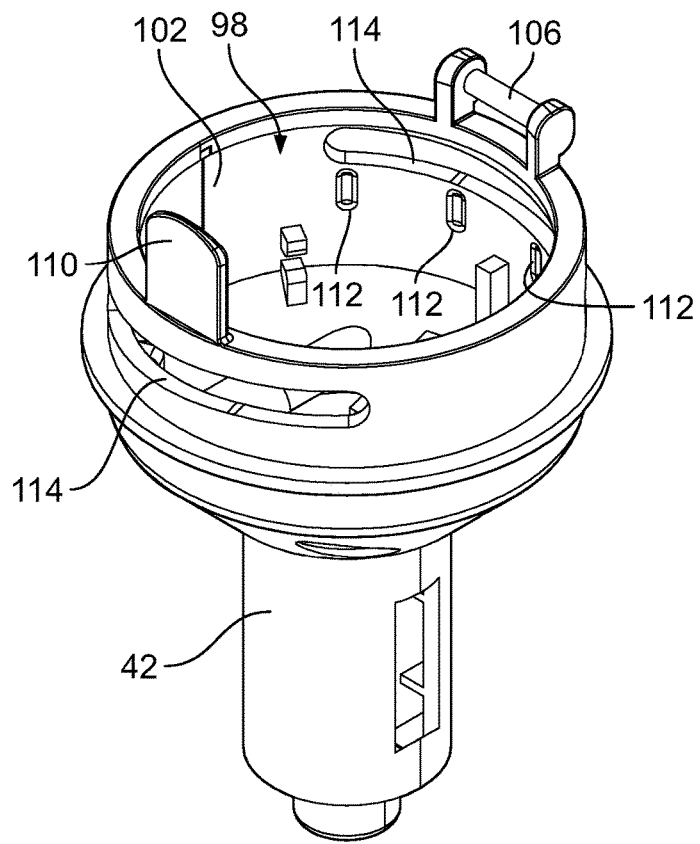
FIG. 7 is a top right isometric view of a body of the air freshener of FIG. 1.
Figure 8:
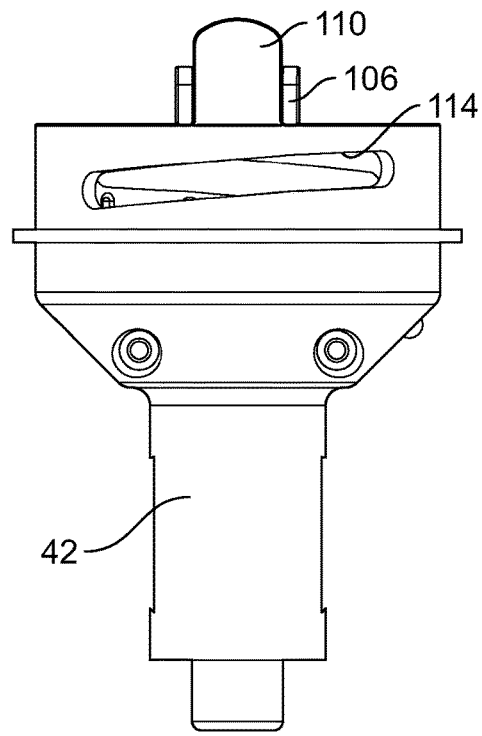
FIG. 8 is a front elevational view of the body of FIG. 7.

The adjustment assembly 38 includes an adjustment ring 70 (see FIG. 6), a cartridge holder 74 (see FIGS. 9 and 10), and portions of the body 42 (see FIGS. 7 and 8). As shown in FIG. 6, the adjustment ring 70 includes a ring cavity 76 defined by a ring inner wall 78, an outer gripping surface 82, a position indicator in the form of a pointer 86, two diametrically opposed apertures 90, and two corresponding diametrically opposed retainers 94 (one visible in FIG. 6).

As shown in FIGS. 7 and 8, the body 42 includes a body cavity 98 defined by a body inner wall 102, a body hinge member in the form of an axle 106 sized to be engaged by the hooks 54 of the lid 34, a latch member 110 arranged to selectively engage the lid latch 50, a plurality of body vents 112, and a body adjustment feature in the form of two diametrically opposed cam profiles 114. The body adjustment feature forms a part of the adjustment assembly 38 as will be discussed further below. The cam profiles 114 are defined by helical shaped slots formed through the body inner wall 102 and extending radially around about ninety degrees of the body 42. In other embodiments, the cam profiles 114 may define a slope that is different than shown, or may extend farther or less far around the perimeter of the body 42. Alternatively, the body adjustment feature may include a projection, a single cam profile 114 or a stepped profile, for example.

Figure 9:
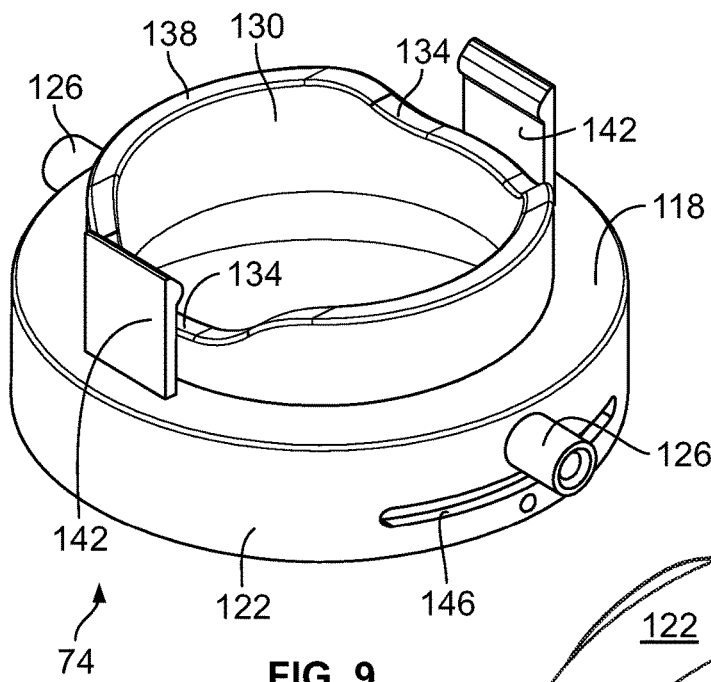
FIG. 9 is a top right isometric view of a cartridge holder of the air freshener of FIG. 1.
Figure 10:
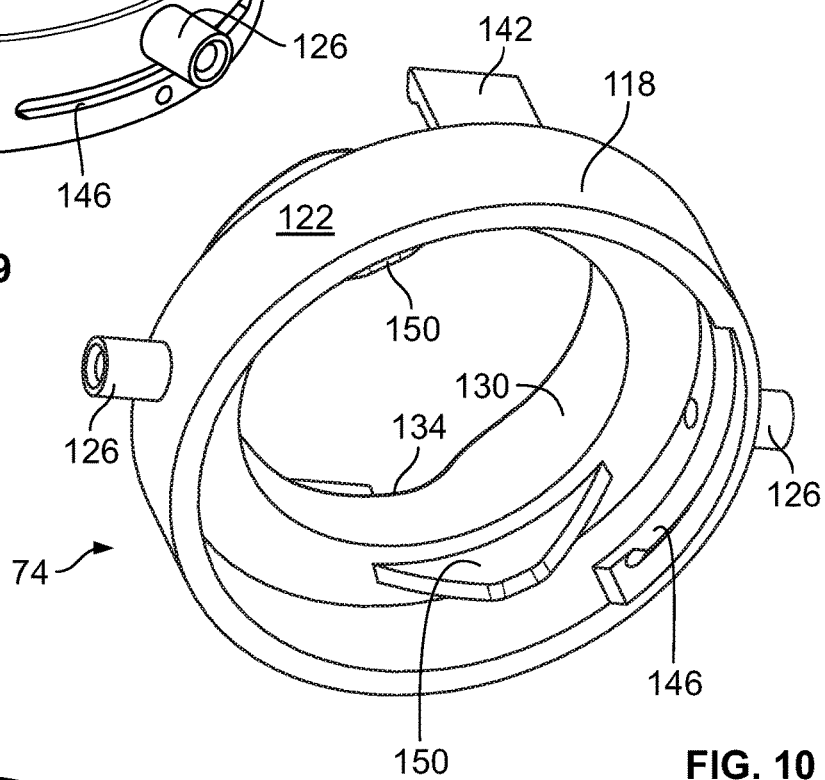
FIG. 10 is a bottom left isometric view of the cartridge holder of FIG. 9.

As shown in FIG. 9, the cartridge holder 74 includes a holder base 118 that defines a holder wall 122 sized to be received within the body inner wall 102, a holder adjustment feature in the form of two diametrically opposed projections 126 sized to be received within the cam profiles 114 of the body 42 and grasped by the retainers 94 and the apertures 90 of the adjustment ring 70, an inner cartridge wall 130 that defines two cutouts 134 and a wall top surface 138, and a cartridge retaining feature in the form of two diametrically opposed clasps 142 that are positioned corresponding to the cutouts 134 of the inner cartridge wall 130. The cartridge holder 74 also includes a vent 146 in the form of an extended slot. The illustrated projections 126 are cylindrical. In other embodiments, the holder adjustment feature may include cam profiles, step profiles, slots, or include one projection, for example. As shown in FIG. 10, the cartridge holder 74 further includes two diametrically opposed switching cams 150.

Figure 11:
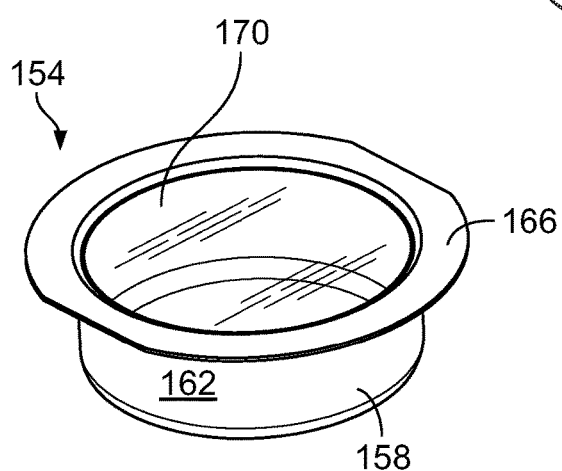
FIG. 11 is a top right isometric view of a cartridge of the air freshener of FIG. 1.

As shown in FIG. 11, a cartridge 154 for use with the air freshener 30 includes a reservoir 158 that defines an outer reservoir wall 162 sized to be received within the inner cartridge wall 130, a flange 166 that extends radially outward from the outer reservoir wall 162 and is sized to be selectively engaged by the clasps 142 (discussed below), and a semi-permeable membrane 170 that isolates the reservoir 158. The reservoir 158 is filled with an active ingredient or volatile material comprising one or more components that is releasable to a local atmosphere through the membrane 170. The active ingredient or volatile material is provided within a carrier material, which together are held within the reservoir 158 as a thickened liquid, gel, oil, etc. It is preferred that the membrane 170 be vapor permeable as opposed to liquid permeable and that it provides for the controlled release of all or a portion of the active ingredient or volatile material therethrough and into the ambient atmosphere (for example, in an automobile cabin). The active ingredient or volatile material can be a fragrance, insecticide, or other product disposed within a carrier liquid, a deodorizing liquid, or the like. For example, the fluid may comprise OUST™, an air and carpet sanitizer for household, commercial, and institutional use, or GLADE®, a household deodorant, both sold by S. C. Johnson and Son, Inc., of Racine, Wis. The fluid may also comprise other actives, such as sanitizers, air and/or fabric fresheners, cleaners, odor eliminators, mold or mildew inhibitors, insect repellents, and the like, or that have aromatherapeutic properties.

In one embodiment, the reservoir 158 is made of one or more polymer layers. The bottom stock can be resilient enough to fit into the cartridge holder 74 and be retained therein. The polymer layers of the reservoir 158 are resilient enough to be sealed against the inner cartridge wall 130 of the cartridge holder 74, retained therein, and heated by the heaters 202 without cracking, tearing, or suffering the effects of repeated heating. In some embodiments, the reservoir 158 may be a deformable reservoir or provide a life indicator that helps the user know when the fragrance oil is running out.

Figure 12:
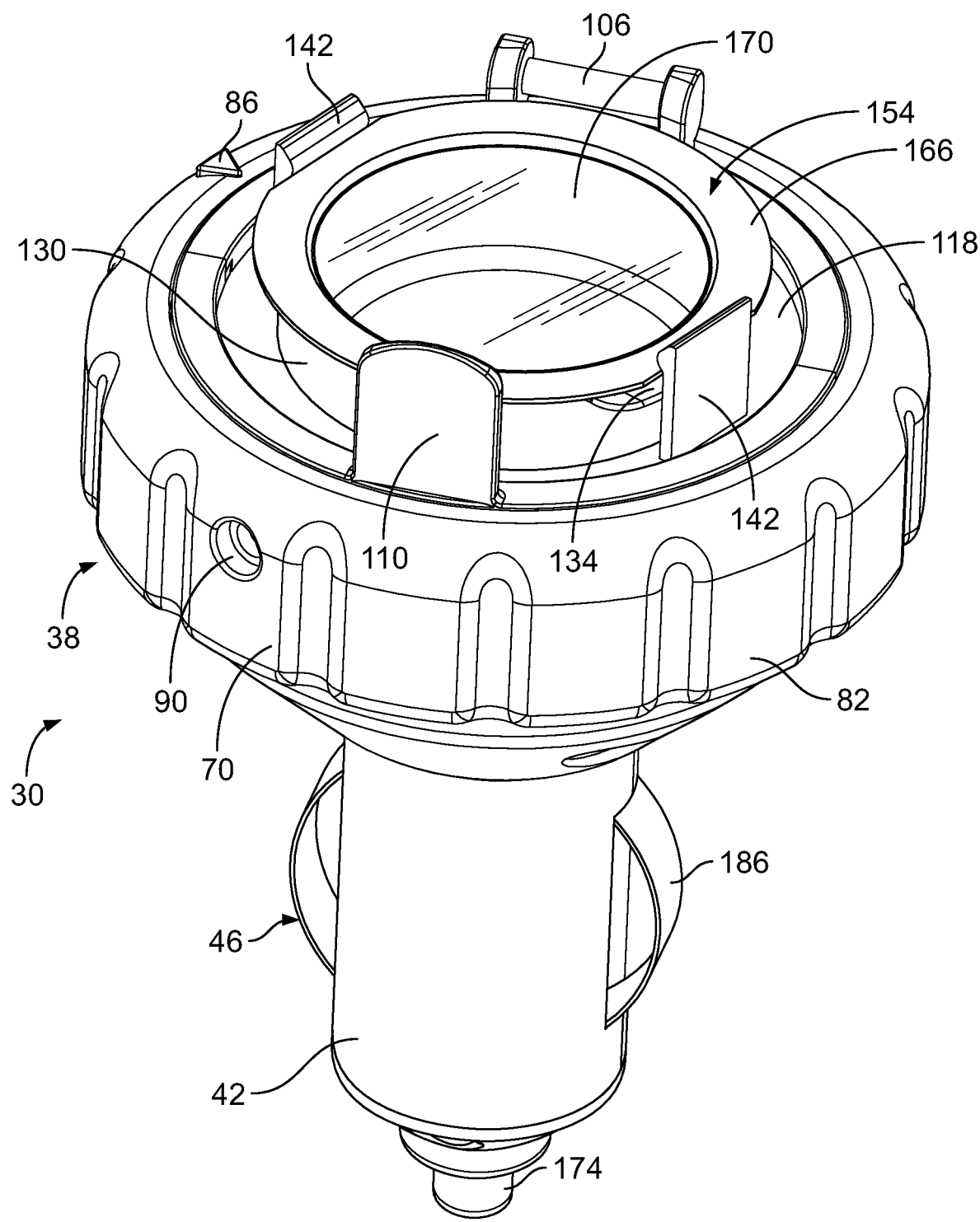
FIG. 12 is a top right isometric view of the air freshener of FIG. 1 with a lid removed.

As shown in FIG. 12, when the air freshener 30 is assembled and the lid 34 opened (or removed as shown in FIG. 12), a user has full access to the cartridge 154, which makes replacement easy as will be discussed below.

Figure 13:
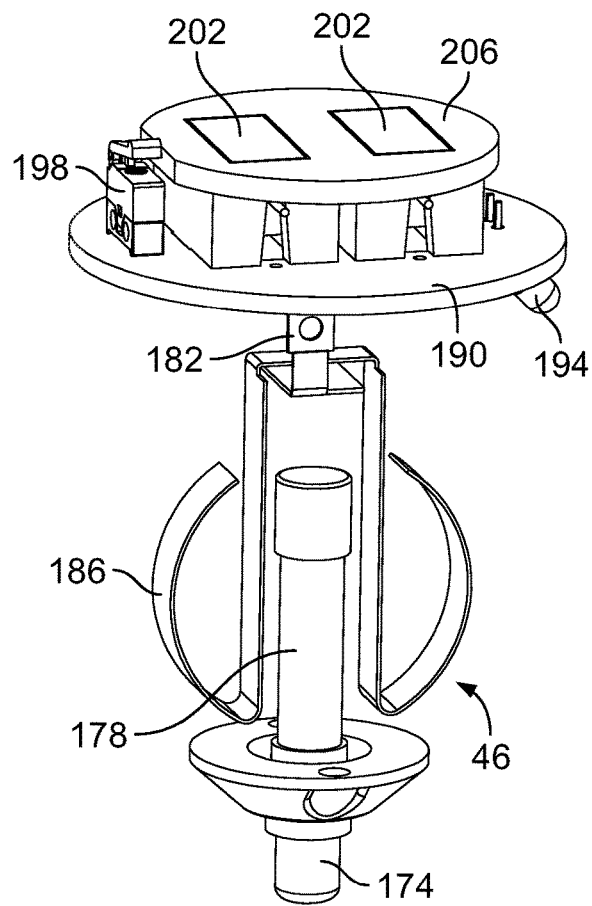
FIG. 13 is a top left isometric view of an electrical system of the air freshener of FIG. 1.
Figure 14:
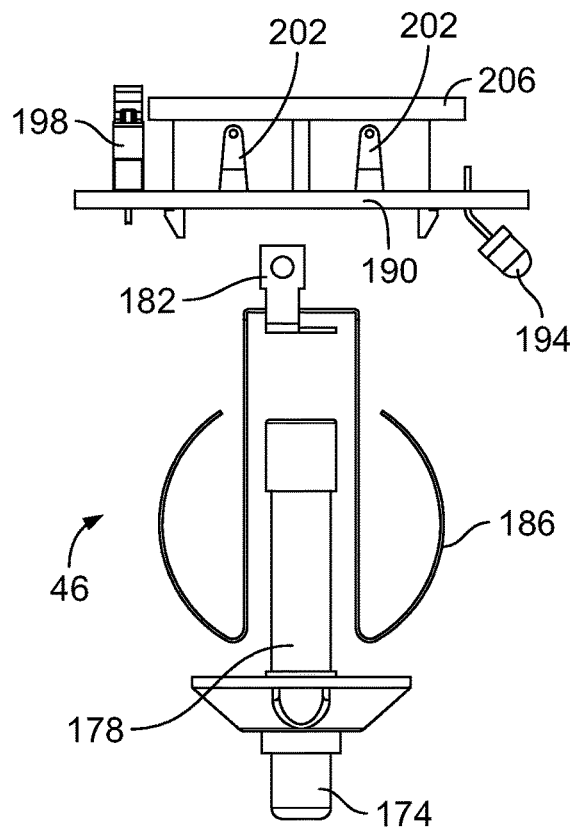
FIG. 14 is a front elevational view of the electrical system of FIG. 13.

Turning to FIGS. 13 and 14, the electrical system 46 includes a positive contact 174, a fuse 178, a positive post 182, a common contact 186, a printed circuit board (PCB) 190 in electrical communication with the positive post 182 and the common contact 186 (connection not shown), an indicator LED 194, a switch 198, two resistive heaters 202, and a heat plate 206 that houses the heaters 202 and couples to the PCB 190. The positive contact 174 and the fuse 178 are movable relative to the positive post 182 to provide selective power to the positive post 182. The switch 198 is arranged to selectively provide power to the heaters 202. The indicator LED 194 is arranged to light up when power is provided to the positive post 182. In other embodiments, the heaters 202 may be film heaters, foil or coil type resistive heaters, or another type of heater capable of providing a temperature increase over ambient in response to provided electrical power.

Figure 15:
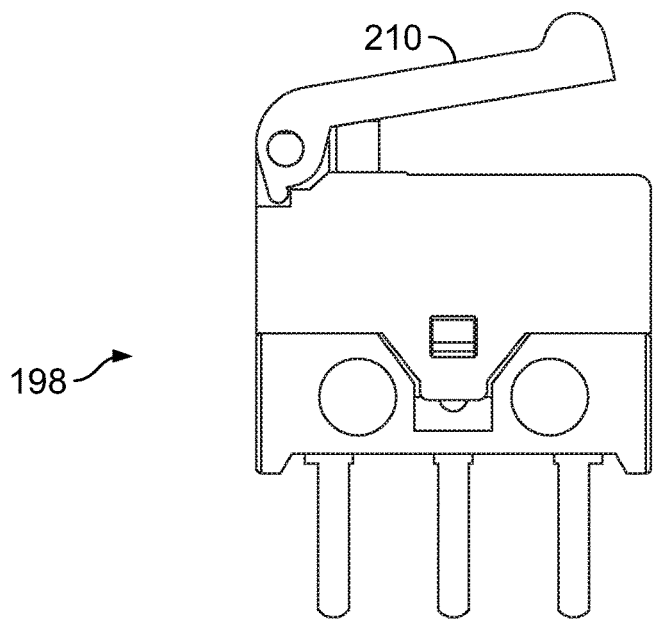
FIG. 15 is an enlarged left side elevational view of a switch of the electrical system of FIG. 13.

As shown in FIG. 15, the switch 198 includes a switch lever 210 that is actuatable between an off position (shown in FIG. 15) that inhibits electrical energy from flowing to the heaters 202 and an on position (shown in FIG. 22) that provides electrical energy to the heaters 202.

Figure 16:
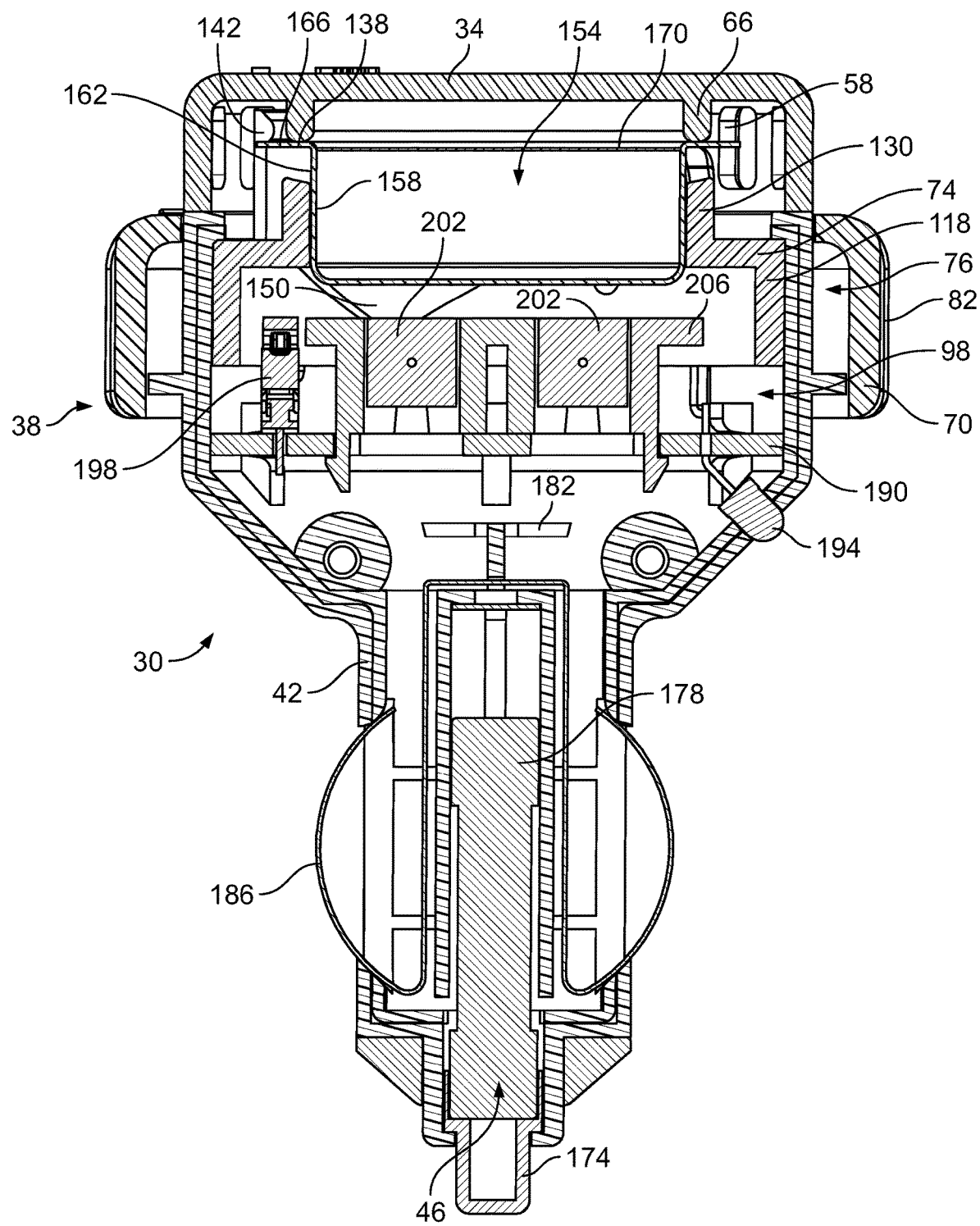
FIG. 16 is a sectional view of the air freshener of FIG. 1 taken along the line 16-16 of FIG. 1.
Figure 17:
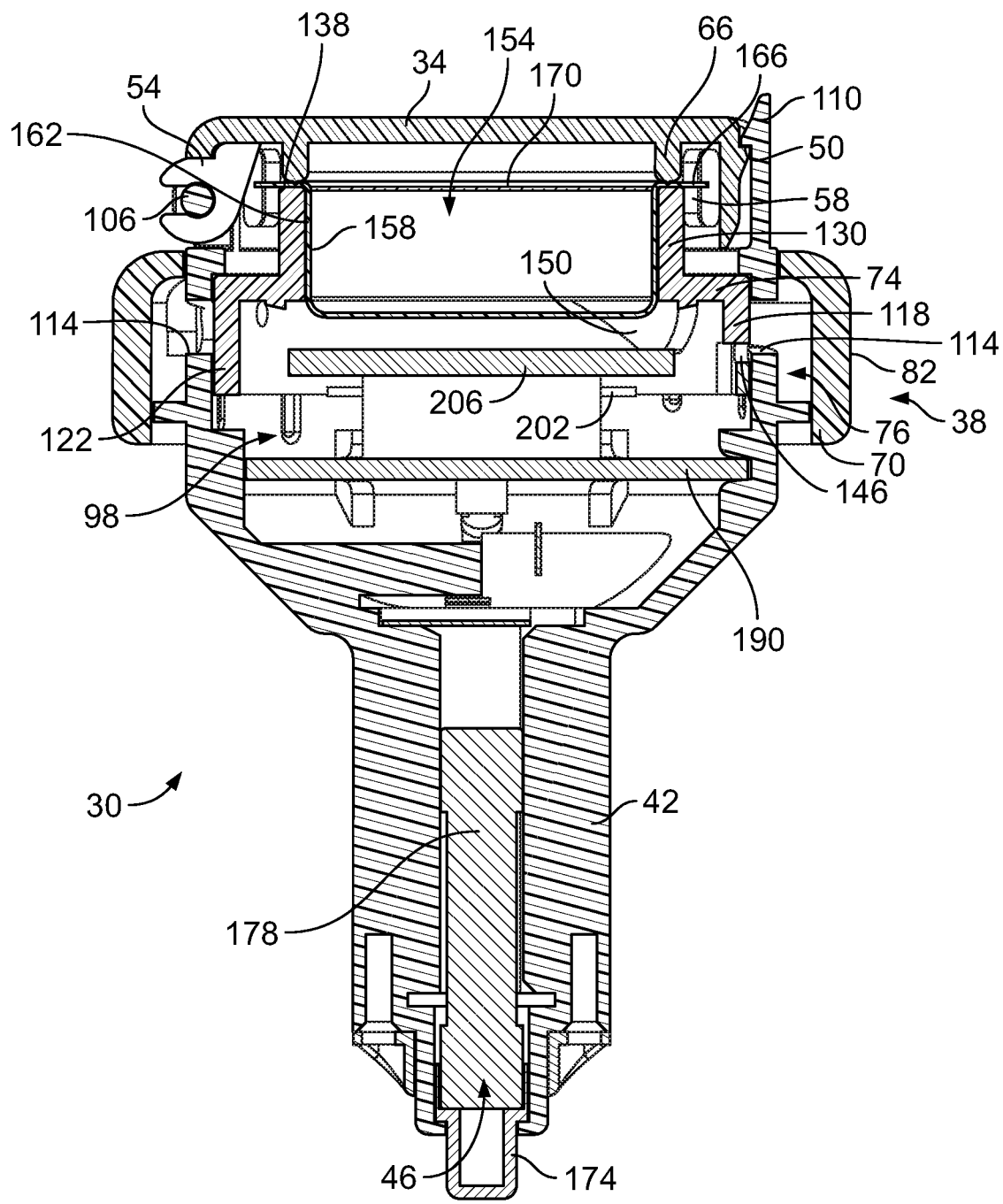
FIG. 17 is a sectional view of the air freshener of FIG. 1 taken along the line 17-17 of FIG. 1.

Assembly of the air freshener 30 will be described below with respect to FIGS. 16 and 17. The electrical system 46 is installed into the body 42 such that the PCB 190 and components mounted thereon are received in the body cavity 98, the LED 194 is visible through the body 42, and the positive contact 174 and common contact 186 extend outside of the body 42. The cartridge holder 74 is also received within the body cavity 98 with the projections 126 received within the cam profiles 114 and the vent 146 aligned with the body vents 112. The body 42 is inserted into the ring cavity 76 of the adjustment ring 70 and the projections 126 on the cartridge holder 74 are engaged by the retainers 94. The cartridge 154 is then inserted into the inner cartridge wall 130 of the cartridge holder 74 with the flange 166 resting on the top surface 138 and the clasps 142 engaged over the flange 166 to maintain the cartridge 154 in place. In one embodiment, the outer reservoir wall 162 provides a light interference fit with the inner cartridge wall 130 of the cartridge holder 74. The lid 34 is then coupled to the body 42 by engaging the hook 54 with the axle 106.

In operation, the air freshener 30 is used with a standard 12V power socket such as those commonly found in automobiles. The body 42 is inserted into the 12V power socket such that the positive contact 174 and fuse 178 are moved into contact with the positive post 182, as is known, and power is provided to the PCB 190. When power is provided to the PCB 190, the LED 194 will glow indicating that the air freshener 30 is receiving power.

The lid 34 is actuatable between a closed position (shown in FIG. 17) where the latch member 110 of the body 42 engages the lid latch 50 to inhibit the lid 34 from leaving the closed position, and an open position (shown in FIG. 18) where the latch member 110 is deflected to release the lid latch 50 allowing the lid 34 to be rotated to the open position about the axle 106. In other embodiments, the lid 34 may move between open and closed positions by a sliding connection, a threaded connection, or another type of retainer that provides selective access to the body cavity 98 and more specifically provides a user with access and the ability to change the cartridge 154.

Figure 19:
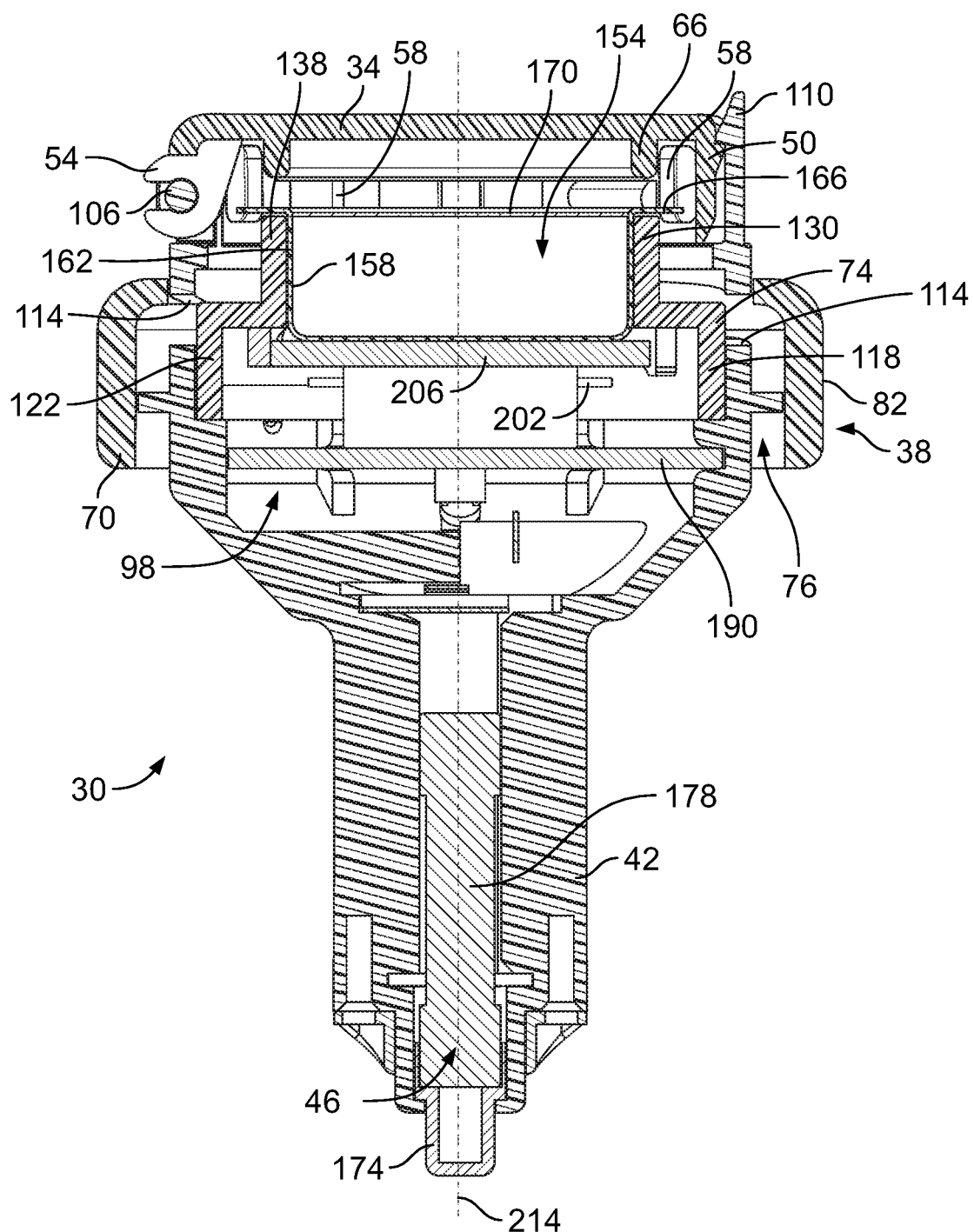
FIG. 19 is a sectional view of the air freshener of FIG. 1 taken along the line 17-17 of FIG. 1 arranged in a first position.

With reference to FIG. 19, the air freshener 30 is shown in a first or maximum output position where the adjustment assembly 38 is adjusted to provide maximum dispersion of the active ingredient out of the cartridge reservoir 158 through the membrane 170. In the maximum output position, the adjustment ring 70 is rotated such that the arrow 86 is aligned with the maximum indicator mark 62 (see FIG. 3). Correspondingly, the cartridge holder 74 is moved within the cam profile 114 such that the cartridge holder 74, and therefore the cartridge 154, are brought into close proximity to the heaters 202 and the heat plate 206 of the electrical assembly 46. In the illustrated embodiment, the cartridge 154 contacts the heaters 202 and the heat plate 206 in the maximum output position. In alternative embodiments, a heater space is provided between the heaters 202 and the cartridge 154 in the maximum output position. The heater space may also be characterized as having a length about a longitudinal axis 214 of the air freshener 30 between about zero and 1.00 millimeters. A head space greater than zero is also provided with a particular uninterrupted volume devoid of structure between the membrane 170 and the lid seal 66 and/or an underside of the lid 34.

Figure 22:
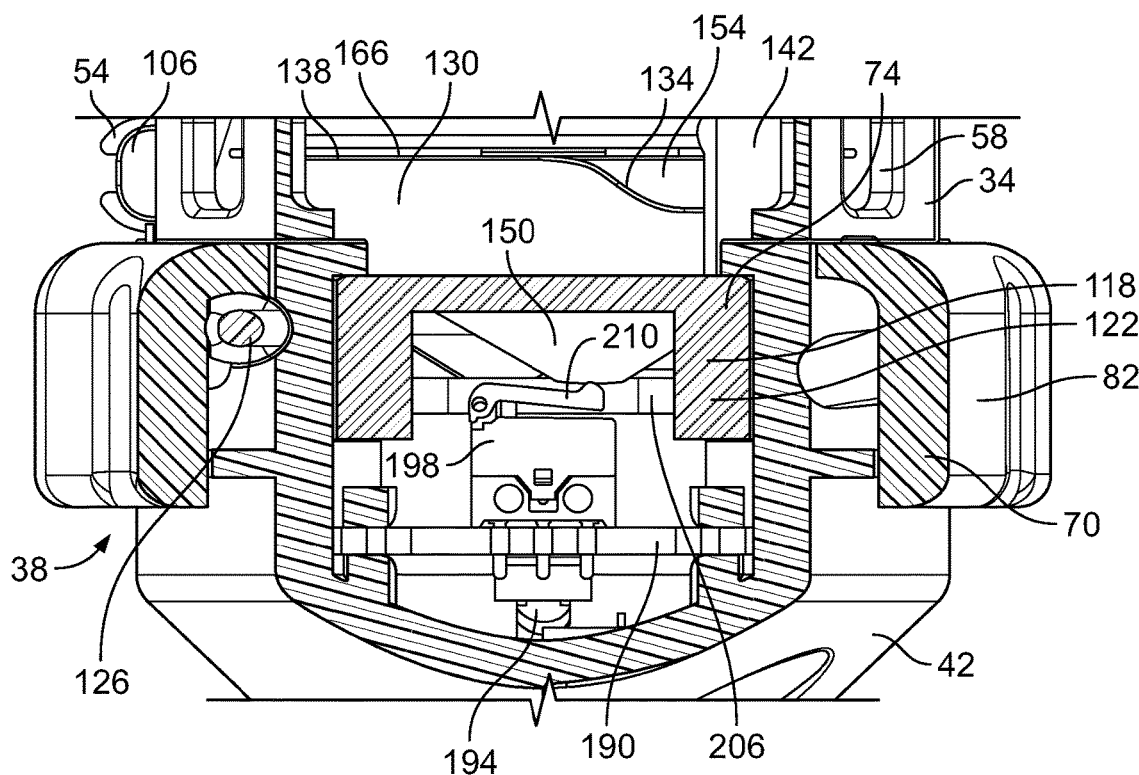
FIG. 22 is a cut away view of the air freshener of FIG. 1 arranged in the third position and showing the switch of FIG. 15.

While in the maximum output position, one of the switching cams 150 of the cartridge holder 74 engages the switch 198 such that power is provided from the positive post 182 to the heaters 202. FIG. 22 clearly shows the switching cam 150 contacting the lever 210 of the switch 198 such that the switch 198 provides power to the heaters 202 in the maximum output position.

In the maximum output position, the cartridge 154 is spaced apart from the lid seal 66 by a maximum cartridge spacing such that air flow is provided from the cartridge 154 to the lid vents 58. The maximum cartridge spacing provides a relatively large head space and flow path for active ingredient released through the membrane 170 to exit the lid vents 58 and diffuse into the surrounding atmosphere. In the maximum output position, the inner cartridge wall 130 does not substantially occlude the vents 58 of the lid 34.

Figure 20:
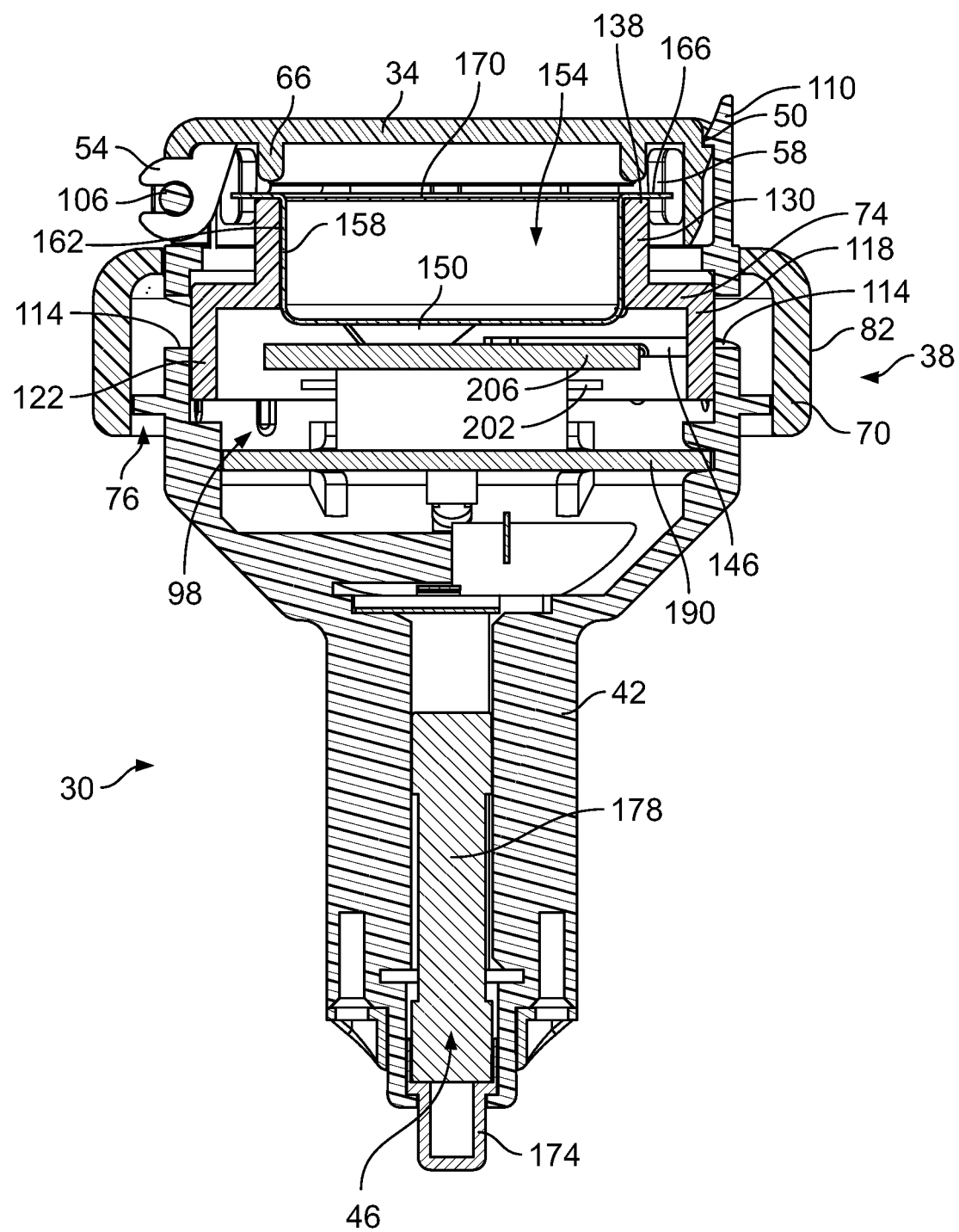
FIG. 20 is a sectional view of the air freshener of FIG. 1 taken along the line 17-17 of FIG. 1 arranged in a second position.

Turning to FIG. 20, the air freshener 30 is shown in a second or intermediate output position where the adjustment assembly 38 is adjusted to provide dispersion of the active ingredient out of the cartridge reservoir 158 through the membrane 170 at a rate between the maximum level discussed above and a minimum level. In the intermediate output position, the adjustment ring 70 is rotated such that the arrow 86 is aligned between the maximum indicator mark 62 and the minimum indicator mark 62 (see FIG. 3). Correspondingly, the cartridge holder 74 is moved within the cam profile 114 such that the cartridge holder 74 and therefore the cartridge 154 are brought farther away from the heaters 202 and the heat plate 206 of the electrical assembly 46 when compared to the maximum output position. In the illustrated embodiment, the cartridge 154 is preferably spaced from the heaters 202 and the heat plate 206 in the intermediate output position by a heater space that is between the maximum output heater space discussed above, and a minimum output heater space that defines a largest spacing between the heaters 202 and the cartridge 154.

Correspondingly, the intermediate output position defines a head space volume between the lid 34 and the cartridge 154 that is less than the head space volume defined at the maximum output position. In the intermediate output position, the inner cartridge wall 130 partially occludes the vents 58 of the lid 34 such that the flow path provided for air exchange between the cartridge 154 and the outside atmosphere is reduced relative to the maximum output position. In this way, the adjustment assembly 38 provides synchronicity between the heat exchange rate provided between the cartridge 154 and the heaters 202 and the size of the flow path provided between the cartridge 154 and the vents 58. Both of these features aid in providing adjustability of fragrance (or other active) delivery.

While in the intermediate output position, the switching cam 150 of the cartridge holder 74 still engages the switch 198 such that power is provided from the positive post 182 to the heaters 202. Further, the cartridge 154 is spaced apart from the lid seal 66 by an intermediate cartridge spacing such that a smaller head space is provided while still allowing for air flow to dispense the active ingredient from the cartridge 154 and through the lid vents 58. The intermediate cartridge spacing provides a smaller flow path than the maximum cartridge spacing for active ingredient released through the membrane 170 to exit the lid vents 58 and diffuse into the surrounding atmosphere.

Figure 21:
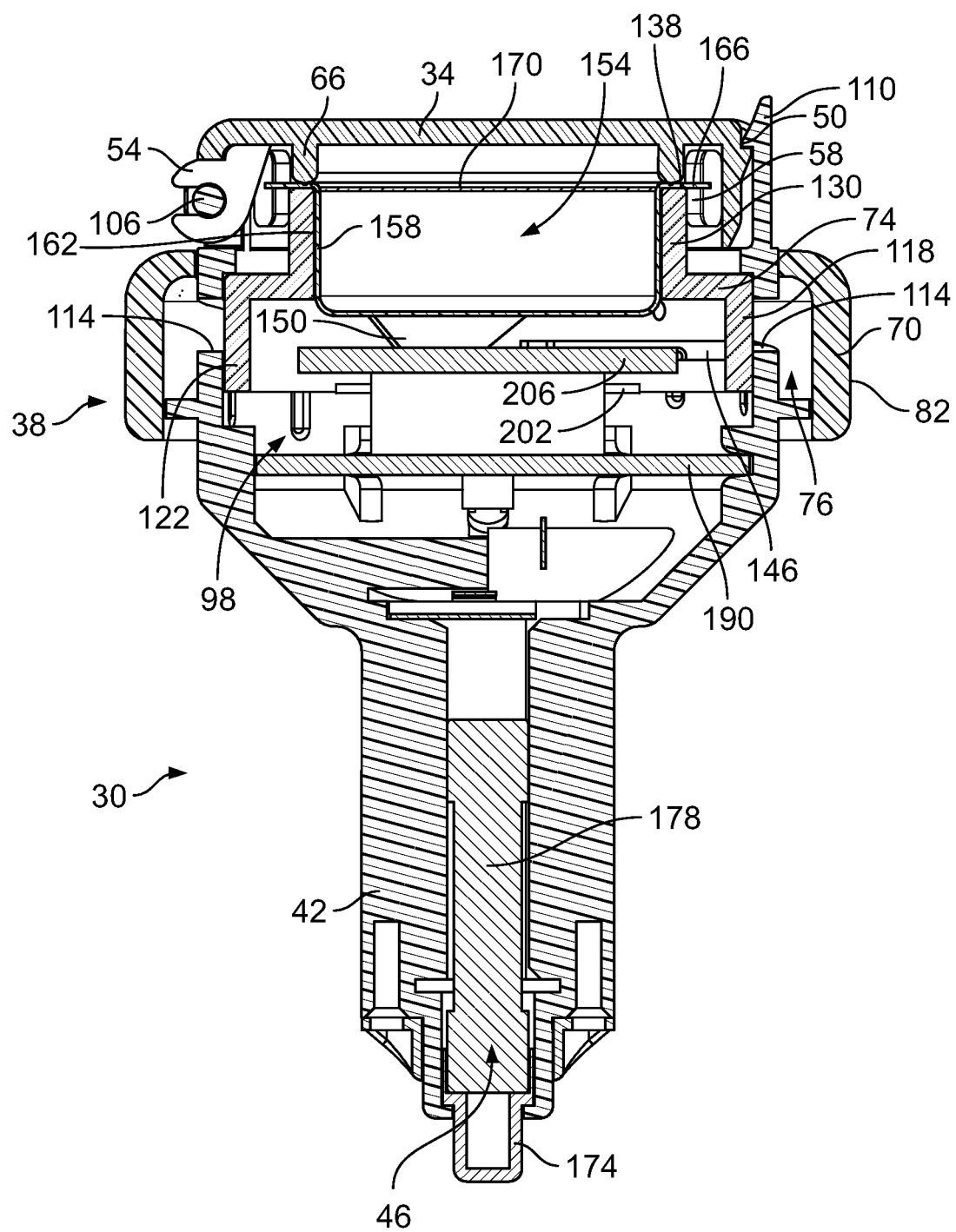
FIG. 21 is a sectional view of the air freshener of FIG. 1 taken along the line 17-17 of FIG. 1 arranged in a third position.

Turning to FIG. 21, the air freshener 30 is shown in a third or off position where the adjustment assembly 38 is adjusted to inhibit dispersion of the active ingredient out of the cartridge reservoir 158 through the membrane 170. In the off position, the adjustment ring 70 is rotated such that the arrow 86 is aligned with the off indicator mark 62 (see FIG. 3). Correspondingly, the cartridge holder 74 is moved within the cam profile 114 such that the cartridge holder 74 and therefore the cartridge 154 are brought a maximum distance away from the heaters 202 and the heat plate 206. Further, the switching cam 150 of the cartridge holder 74 disengages the switch 198 (see FIGS. 15 and 22) to interrupt power flow between the positive post 182 and the heaters 202, such that the heaters 202 do not provide substantial (or any) heat. In the off position, the cartridge 154 is brought into engagement with the lid seal 66. The lid seal 66 contacts the flange 166 and inhibits air flow between the lid vents 58 and the cartridge 154.

The user has the option of manipulating the adjustment ring 70 to the maximum output position to provide a relatively large amount of active into the atmosphere, the intermediate output position to maintain a desired amount of active in the atmosphere or to provide a more subtle level of active (for example, a subtle fragrance level), and the off position to eliminate the diffusion of active into the atmosphere or to save the cartridge 154 from being used up while the user is not near the air freshener 30. The relative size of the flow path provided between the cartridge 154 and the vents 58 of the lid 34 is synchronized with the heat exchange rate provided between the cartridge 154 and the heaters 202.

Figure 18:
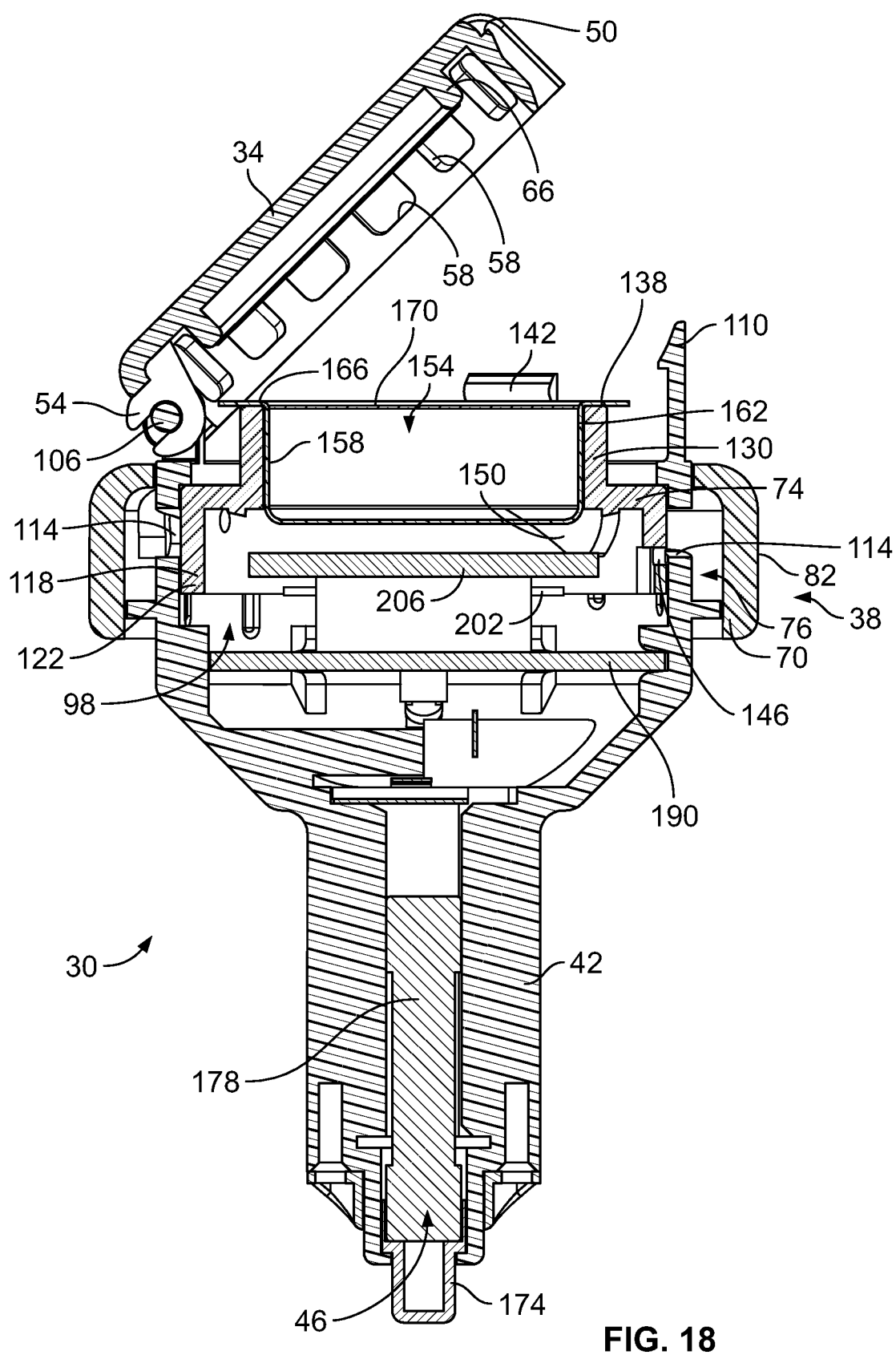
FIG. 18 is a sectional view of the air freshener of FIG. 1 taken along the line 17-17 of FIG. 1 with the lid in an open position.

With reference to FIG. 18, when the active ingredient within the cartridge 154 is spent (or substantially used up or otherwise no longer effective for its intended purpose), the user replaces the cartridge 154 by opening the lid 34, deflecting the clasps 142 of the cartridge holder 74, grasping the flange 166 of the cartridge 154, and removing the spent cartridge 154. The cartridge 154 is then disposed of, and a new cartridge 154 installed by pressing the new cartridge 154 into the inner cartridge wall 130 of the cartridge holder 74 until the flange 166 of the new cartridge 154 contacts the top surface 138 of the inner cartridge wall 130. The clasps 142 are then engaged with the new cartridge 154, and the lid 34 is moved to the closed position.

Figure 23:
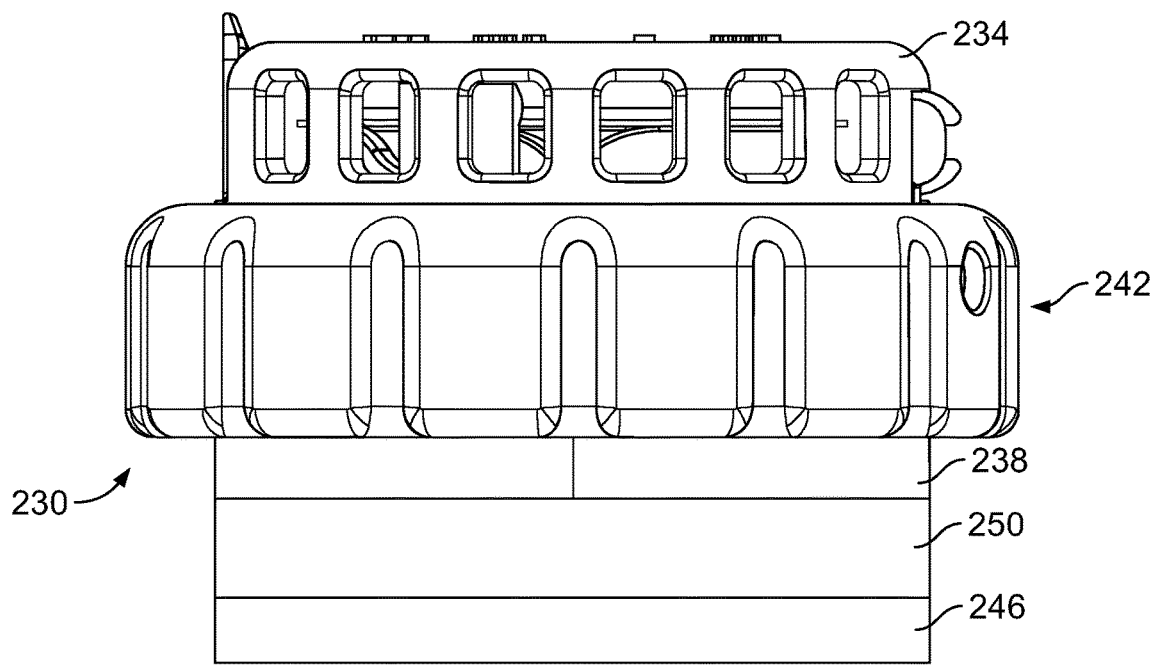
FIG. 23 is a right side elevational view of another air freshener.

FIG. 23 shows an alternative air freshener 230 that includes a lid 234, a body 238, an adjustment assembly 242, a heat source 246, and an attachment mechanism 250. The adjustment assembly 242 functions the same way as described above and includes similar parts. The heat source 242 may be an automobile heating vent or another heat source that is not electrically driven from within the air freshener 230. The attachment mechanism 250 can be a clip that holds the air freshener 230 in place, for example on the automobile heating vent. In the embodiment shown in FIG. 23, the maximum output position may provide more heat exchange between the heat source 246 and the cartridge 154 while providing maximum air exchange with the cartridge 154. The intermediate output position may provide a heat exchange rate between the maximum and a minimum heat exchange rate and provide relatively less air flow to the cartridge than the maximum output position. The off position may seal the cartridge 154 or otherwise inhibit air flow to the cartridge 154 while minimizing the heat exchange rate between the heat source 246 and the cartridge 154.

The above described air fresheners provide a device that allows the user to maintain a pleasant level of active (e.g., fragrance) in the atmosphere by controlling a rate of active release between a maximum and a minimum level, and also provides a shut off feature that saves the active from being wasted and unwanted active release from occurring at unwanted times.

In other embodiments, the flange 166 of the cartridge 154 may be eliminated. The cartridge 154 may be held in the cartridge holder 74 by an interference fit, a clasp, or another retainer as desired. Additionally, the lid seal 66 may engage and effectively seal against the top surface 138 of the inner cartridge wall 130 instead of the flange 166. In yet another embodiment, the lid seal 66 is fashioned to completely cover and contact the membrane 170 to prevent active emission. Alternatively, the adjustment assembly 38 may include a component that seals the lid vents 58 instead of sealing against the flange 166 or the top surface 138. Regardless of how effected, the adjustment assembly 38 isolates the cartridge 154 from the outside atmosphere when the air freshener 30, 230 is in the off position.

In other embodiments, the air freshener may be arranged with sliding actuation of the lid. Additionally, the adjustment mechanism may include a linear slide type actuation, as opposed to the rotary actuation illustrated.

Any of the embodiments described herein may be modified to include any of the structures or methodologies disclosed in connection with different embodiments. Further, the present disclosure is not limited to air fresheners for use in automobiles but may apply to AC mains powered devices for releasing an active ingredient into an atmosphere or other devices that release an active ingredient into the atmosphere.

INDUSTRIAL APPLICABILITY

An air freshener is presented that is controllable between a maximum output position, an intermediate output position, and an off position to provide a desirable level of active release. The air freshener includes an adjustment assembly that varies the air flow provided between a cartridge and the atmosphere and a rate of heat exchange with the cartridge, and also provides an off position where air flow is inhibited to the cartridge.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. An automobile air freshener, comprising:
    a housing arranged to be received within a 12V power socket;
    an electrical system received within the housing and arranged to receive power from the 12V power socket, the electrical system including a heater and a switch selectively powering the heater;
    an adjustment assembly movable in a linear and rotational direction between an on position and an off position, and including a cartridge holder movable with the adjustment assembly and configured to hold a cartridge, the adjustment assembly arranged to actuate the switch when in the on position such that power is supplied to the heater; and
    a lid including a lid seal arranged to inhibit air flow to the cartridge when the adjustment assembly is in the off position,
    wherein the cartridge holder, the cartridge, and the adjustment assembly are movable in the linear and rotational direction along a cam profile, and wherein the cam profile is defined by a slot formed through the housing.

2. The automobile air freshener of claim 1, wherein the lid includes lid vents for providing air flow between an ambient atmosphere and the cartridge when the adjustment assembly is arranged in the on position.

3. The automobile air freshener of claim 1, wherein when the adjustment assembly is arranged in the off position the switch inhibits power from being supplied to the heater, even when the electrical system is receiving power from the 12V power socket.

4. The automobile air freshener of claim 1, wherein the lid seal inhibits volatile emission from the cartridge when the adjustment assembly is in the off position even when the electrical system is receiving power from the 12V power socket.

5. An adjustment assembly for a volatile material configured to interact with a heat source, the adjustment assembly comprising:
an adjustment ring graspable by a user and actuatable between a maximum output position, an intermediate output position, and an off position; and
a cartridge holder arranged to hold a cartridge that includes a semi permeable membrane and a reservoir filled with an active ingredient, the cartridge coupled to and movable in a linear and rotational direction with the adjustment ring along a cam profile such that when arranged in the maximum output position a maximum heat exchange rate between the heat source and the cartridge is achieved, when arranged in the off position a minimum heat exchange rate between the heat source and the cartridge is achieved, and when arranged in the intermediate output position an intermediate heat exchange rate is achieved that is between the maximum heat exchange rate and the minimum heat exchange rate,
wherein the cartridge holder includes a projection for securing the adjustment ring to the cartridge holder.

6. The adjustment assembly of claim 5, further comprising a cartridge that includes a semi permeable membrane and a reservoir filled with an active ingredient.

7. The adjustment assembly of claim 5, wherein the adjustment ring is rotatable between the maximum output position, the intermediate output position, and the off position.

8. The adjustment assembly of claim 5, wherein the cartridge is positioned closer to the heat source in the maximum output position than in the intermediate output position, and the cartridge is positioned closer to the heat source in the intermediate output position than in the off position.

9. The adjustment assembly of claim 5, wherein air flow to the cartridge is inhibited in the off position.

10. The adjustment assembly of claim 5, wherein the adjustment assembly controls a flow of electrical power to the heat source.

11. A volatile material dispenser, comprising:
a housing;
an electrical assembly received within the housing and including a heater; and
an adjustment assembly coupled to the housing and configured to support a cartridge, the adjustment assembly and the cartridge movable in a linear and rotational direction away from the heater along a cam profile between a maximum output position, an intermediate output position, and an off position,
wherein the cam profile is defined by a slot formed through the housing.

12. The volatile material dispenser of claim 11, wherein the electrical assembly includes a switch arranged to provide selective electric power to the heater, and the adjustment assembly actuates the switch such that power is provided to the heater when the adjustment assembly is not in the off position.

13. The volatile material dispenser of claim 11, wherein the adjustment assembly varies the release rate of an active from the cartridge and turns off the heater.

14. The volatile material dispenser of claim 11, wherein the adjustment assembly further includes a cartridge holder arranged to support the cartridge, and that interacts with the housing to move along the cam profile between the maximum output position, the intermediate output position, and the off position, wherein the cam profile is helical.

15. The volatile material dispenser of claim 14, wherein the cartridge holder includes a projection, and
wherein the projection is received within the cam profile.

16. The volatile material dispenser of claim 14, wherein the cartridge holder is arranged to bring the cartridge closer to the heater when the adjustment assembly is arranged in the maximum output position, and farther away from the heater when the adjustment assembly is arranged in the intermediate output position.

17. The volatile material dispenser of claim 11, wherein the adjustment assembly synchronizes a relative size of a flow path provided between the cartridge and an atmosphere outside the volatile material dispenser, and a heater space provided between the heater and the cartridge.

18. The volatile material dispenser of claim 11, wherein the adjustment assembly includes an adjustment ring that is actuatable between the maximum output position, the intermediate output position, and the off position, resulting in the movement of the cartridge holder relative to the heater.

19. The volatile material dispenser of claim 11, further comprising a lid movable between an open position and a closed position and selectively encasing the cartridge within the housing, and including a lid seal arranged to selectively inhibit air flow to the cartridge.

* * * * *